US012788237B2

(12) United States Patent
Charles

(10) Patent No.: US 12,788,237 B2
(45) Date of Patent: Nov. 10, 2026

(54) VIEWING CONTACT LENSES WITH INTEGRATED SPECULUMS

(71) Applicant: Alcon Inc., Fribourg (CH)

(72) Inventor: Steven T. Charles, Memphis, TN (US)

(73) Assignee: Alcon Inc., Fribourg (CH)

( * ) Notice: Subject to any disclaimer, the term of this patent is extended or adjusted under 35 U.S.C. 154(b) by 169 days.

(21) Appl. No.: 18/509,776

(22) Filed: Nov. 15, 2023

(65) Prior Publication Data

US 2024/0215814 A1 Jul. 4, 2024

Related U.S. Application Data

(60) Provisional application No. 63/478,368, filed on Jan. 4, 2023.

(51) Int. Cl.
*A61B 1/32* (2006.01)
*A61B 3/125* (2006.01)

(52) U.S. Cl.
CPC ................ *A61B 1/32* (2013.01); *A61B 3/125* (2013.01)

(58) Field of Classification Search
CPC .. A61B 3/12; A61B 3/125; A61B 3/14; A61B 3/0025; A61B 3/10; A61B 1/06; A61B 17/0231; A61B 1/00045; A61B 3/1208; A61B 1/00163; A61B 2560/0443; A61B 3/00; A61B 3/16; A61F 2009/00872; A61F 2009/00853; A61F 2009/0052; G02B 1/043; G02B 27/0068; G02B 21/0052; G02C 7/04; G02C 7/049; G02C 7/083; G02C 2202/24; G02C 7/043
See application file for complete search history.

(56) References Cited

U.S. PATENT DOCUMENTS 4,265,519 A * 5/1981 Pomerantzeff ......... A61B 3/125
351/205
5,309,187 A 5/1994 Crossman
5,589,896 A 12/1996 Mainster
5,623,323 A 4/1997 Johnson
8,836,778 B2 9/2014 Ignatovich
9,339,375 B2 5/2016 Lee
9,744,030 B2 8/2017 Lee
9,801,540 B2 10/2017 Yates
11,406,490 B2 8/2022 Kahook
11,484,198 B2 11/2022 Yao
2006/0055884 A1 3/2006 Molinari
2007/0030448 A1 2/2007 Biernat
(Continued)

FOREIGN PATENT DOCUMENTS

CN 208876529 U 5/2019
EP 1295579 A1 3/2003

*Primary Examiner* — Brandi N Thomas
(74) *Attorney, Agent, or Firm* — PATTERSON + SHERIDAN, LLP

(57) ABSTRACT

Aspects of the present disclosure relate to an integrated contact lens apparatus for ophthalmoscopic examination comprising a lens portion, an upper speculum portion, and a lower speculum portion, and methods of use thereof. The integrated contact lens apparatus facilitates improved visualization of the peripheral retina, including the superior and inferior hemiretinas, via both manual examination and wide-angle cameras that may utilize contact lenses for viewing. The integrated contact lens apparatus further prevents or reduces corneal drying and patient discomfort during examination.

16 Claims, 8 Drawing Sheets

(56) References Cited

U.S. PATENT DOCUMENTS

| | | | | |
|---|---|---|---|---|
| 2007/0282405 | A1 | 12/2007 | Wong | |
| 2017/0340201 | A1 | 11/2017 | Rill | |
| 2022/0031503 | A1* | 2/2022 | Dorin | A61F 9/008 |
| 2023/0414099 | A1 | 12/2023 | Charles | |

* cited by examiner

4120

VIEWING CONTACT LENSES WITH INTEGRATED SPECULUMS

CROSS-REFERENCE TO RELATED APPLICATIONS

This application claims the benefit of priority of U.S. Provisional Patent Application Ser. No. 63/478,368 titled "VIEWING CONTACT LENSES WITH INTEGRATED SPECULUMS," filed on Jan. 4, 2023, which is hereby incorporated by reference in its entirety as though fully and completely set forth herein.

BACKGROUND

During ophthalmic screenings involving ophthalmoscopy or digital imaging techniques, practitioners may use various lenses or tools in an attempt to view the interior of a patient's eye.

Ophthalmoscopy is routinely performed to examine the retina of the eye. One type of ophthalmoscopy is indirect ophthalmoscopy. Indirect ophthalmoscopy is performed using a head-mounted illumination source, an optical system, and a handheld lens, which gathers the light reflected from the back of the eye. This type of examination may take anywhere from 10 to 30 minutes total to examine both eyes of a patient. During this period, the patient is required to refrain from blinking while keeping the examined eye wide open. Also during such examination, the ophthalmologist is often physically very close to the patient being examined so as to view reflection of light from various hemiretina fields, especially the difficult-to-view superior and inferior hemiretinas.

SUMMARY

Problems with indirect ophthalmoscopy include, but are not limited to: limited peripheral retinal visualization due to obstruction by the eyelids and eyelashes; corneal drying, which may lead to patient discomfort and impaired image quality; and involuntary movement of the eye and the eyelids, such as by blinking, rolling of the eye, and squeezing of the muscles around the eye, which are often involuntary responses to the discomfort created by the prolonged examination and exposure of the cornea to air without moisture (either natural or "artificial tears").

Described herein are one or more embodiments of an integrated contact lens apparatus comprising a lens portion, an upper speculum portion, and a lower speculum portion, and methods of use thereof.

The one or more embodiments of an integrated contact lens apparatus enable improved visualization of the peripheral retina, including the superior and inferior hemiretinas, via both manual examination and wide-angle cameras that may utilize contact lenses for viewing. Ultra-wide field digital images are often obstructed by the presence of upper and lower eyelids and eyelashes in the field of view. The integrated contact lens apparatus described herein mitigates or eliminates corneal asphericity, such as those caused by radial keratotomy (RK), penetrating keratoplasty (PKP), laser in situ keratomileusis (LASIK), limbal relaxing incision (LRI), arcuate keratotomies (AK), keratoconus (KCN), and due to corneal lacerations, resulting in improved imaging of the retina. The integrated contact lens apparatus also prevents or reduces corneal drying and reduces patient discomfort. Integrated upper and lower speculum cups of the integrated contact lens apparatus may keep the eyelids open, thereby enabling a more rapid and complete peripheral retinal examination due to lack of involuntary patient movement due to discomfort. This single-use nature of an integrated contact lens apparatus eliminates the disinfecting and cleaning requirements for expensive medical lenses, including hand-held equipment. Avoiding repeated handling, cleansing, and sterilization of optical surfaces prolongs their usefulness. Accordingly, embodiments of the present disclosure provide an apparatus and methods of use thereof for improved ophthalmoscopy, including indirect ophthalmoscopy.

This Summary is not intended to represent every possible embodiment or every aspect of the subject disclosure. Rather, the foregoing summary is intended to exemplify some of the novel aspects and features disclosed. The features and advantages, and other features and advantages of the subject disclosure, will be readily apparent from the following Detailed Description and modes for carrying out the subject disclosure when taken in connection with the accompanying Brief Description of the Drawings and the appended Claims.

BRIEF DESCRIPTION OF THE DRAWINGS

For both the figures and the specification, like numbers refer to like elements throughout.

DETAILED DESCRIPTION

In the following description, details are set forth by way of example to facilitate an understanding of the disclosed subject matter. It should be apparent to a person of ordinary skill in the field, however, that the disclosed implementations are exemplary and not exhaustive of all possible implementations. Thus, it should be understood that the reference to the described examples is not intended to limit the scope of the disclosure. Any alterations and further modifications to the described devices, instruments, methods, and any further application of the principles of the present disclosure are fully contemplated as would normally occur to one skilled in the art to which the disclosure relates. In particular, it is fully contemplated that the features, components, or steps described with respect to one implementation may be combined with the features, components, or steps described with respect to other implementations of the present disclosure.

Figure 1A:
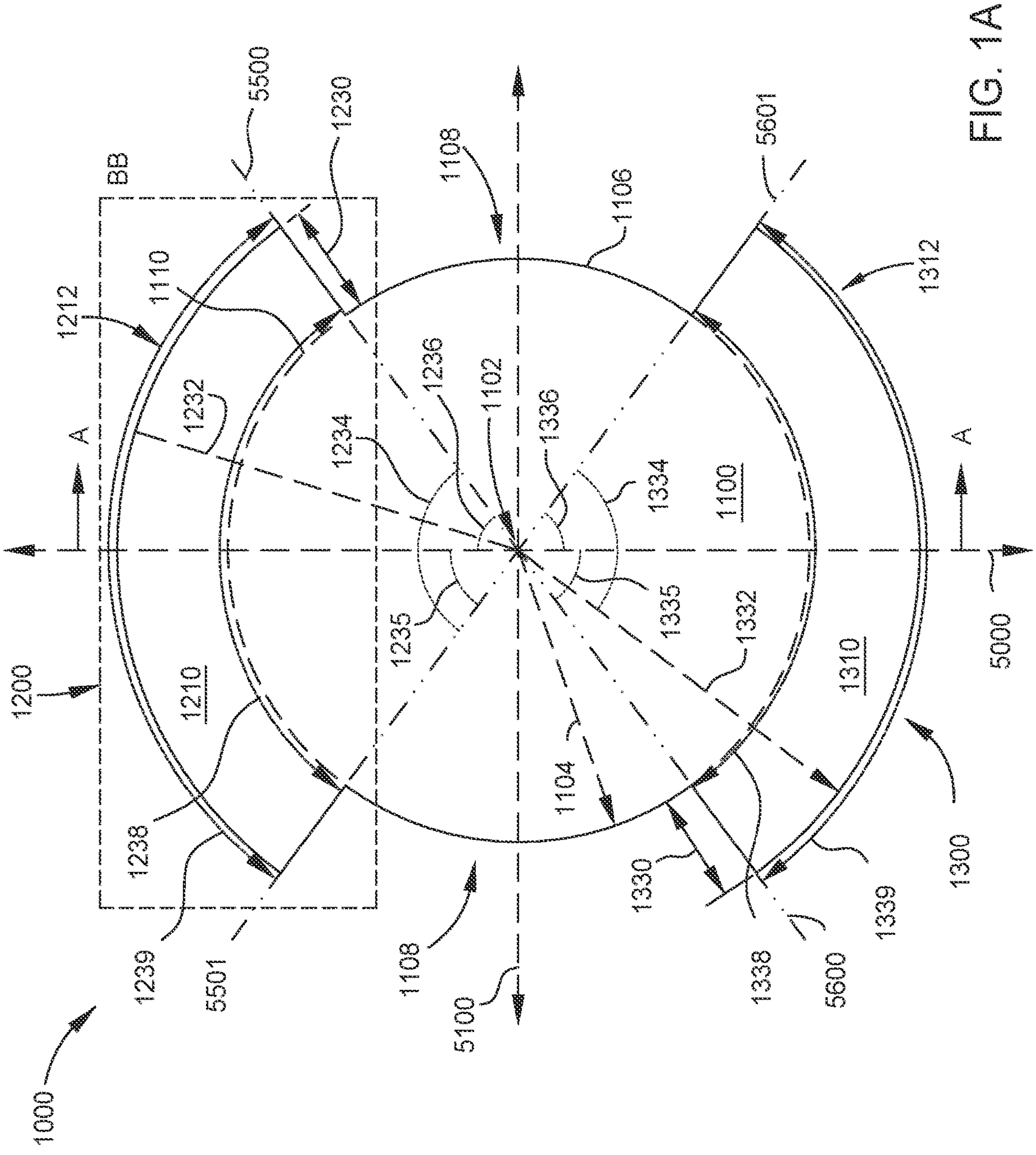
FIG. 1A provides a frontal view of a fully-integrated contact lens apparatus configured for introduction into a human eye, according to one or more embodiments.
Figure 1B:
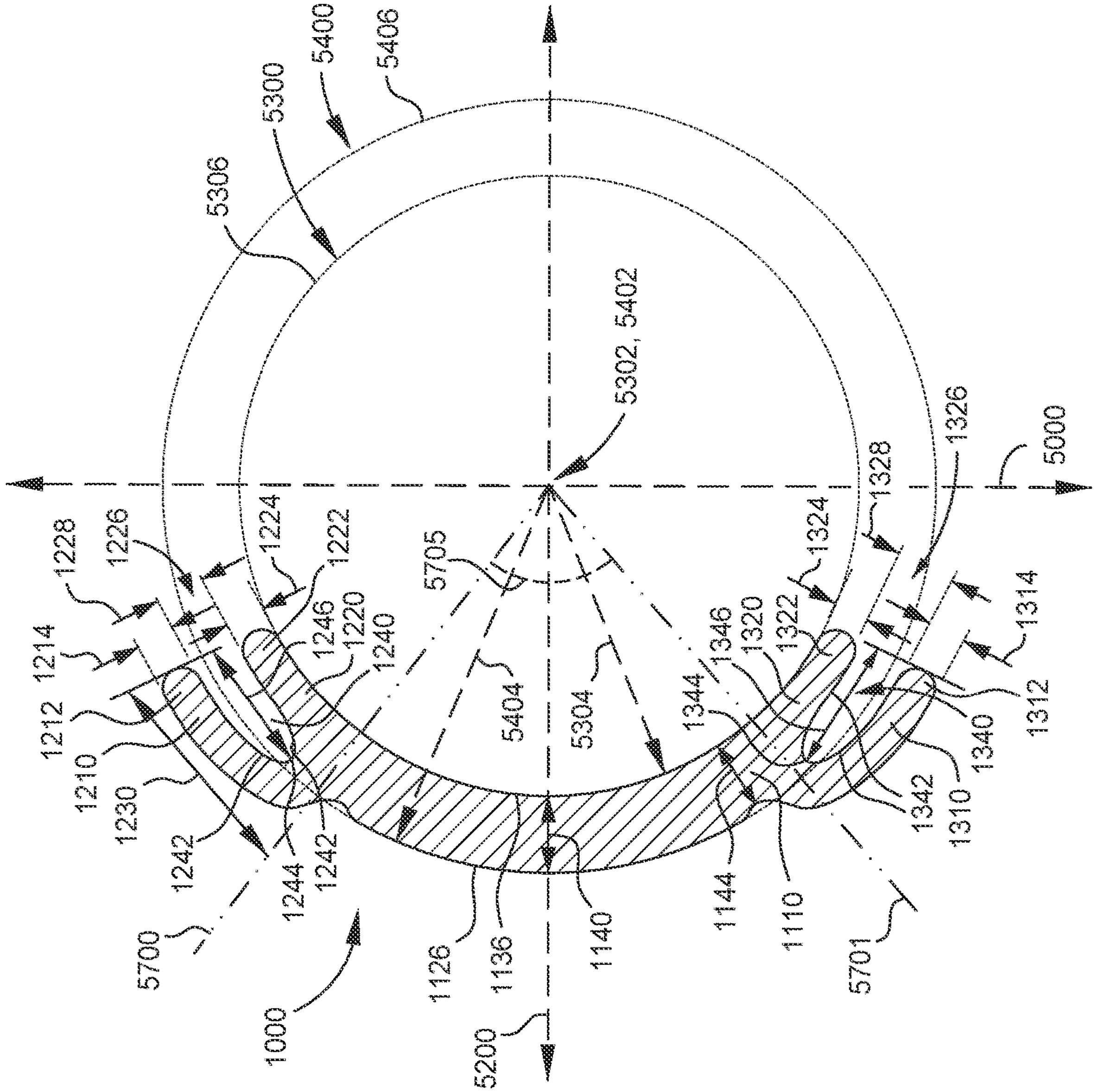
FIG. 1B provides a cross-sectional side view of a fully-integrated contact lens apparatus introduced into an eye as viewed along sight lines AA of FIG. 1A, according to one or more embodiments.
Figure 1C:
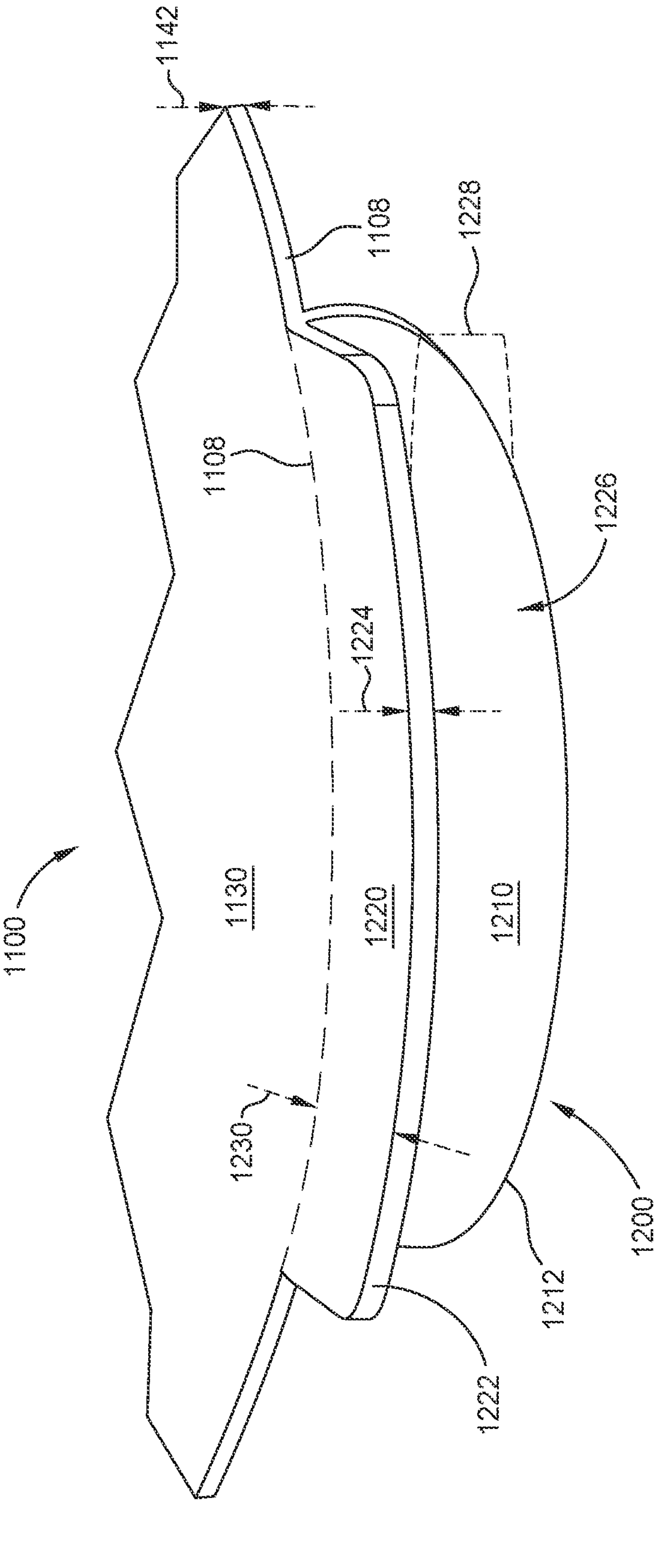
FIG. 1C provides a partial perspective view of a speculum cup of an upper speculum portion according to box BB of FIG. 1A, according to one or more embodiments.

FIGS. 1A-1C illustrate an exemplary fully-integrated contact lens apparatus and portions thereof configured for introduction into a human eye. FIG. 1A provides a frontal view of the fully-integrated contact lens apparatus. FIG. 1B is a cross-sectional side-view of the exemplary fully-integrated contact lens apparatus provided in FIG. 1A along view line AA. FIG. 1C provides a perspective sectional view of the speculum cup of an upper speculum portion of the fully-integrated contact lens apparatus in FIG. 1A along view box BB.

In the context of this application, "fully-integrated" means that the embodiment contact lens apparatus is formed as a singular piece, that is, the entirety of the embodiment contact lens apparatus is whole, seamless, and one, even though "portions", "segments", or "sections" may be differentiated and identified for descriptive purposes. Something that is "fully-integrated" is "integrated" by definition, but an integrated contact lens apparatus may also have a first portion and a second portion that are merged, coupled, connected, or otherwise bonded into a single apparatus using known joining techniques in the art, such as through use of an adhesive, welding, or fastening.

Whether fully-integrated or integrated, a first portion and a second portion of an embodiment contact lens apparatus may comprise the same, similar, or different materials in various portions, segments, or sections of the contact lens apparatus, such as the lens and the speculum portions.

The fully-integrated contact lens apparatus 1000 shown in FIGS. 1A-B comprises a lens 1100, an upper speculum portion 1200, and a lower speculum portion 1300. FIG. 1C shows a section of the lens 1100 and the upper speculum portion 1200.

In viewing FIG. 1A, several axis and angle lines are shown to help define portions of the potential geometry of the fully-integrated contact lens apparatus 1000. A true vertical axis 5000 and a true horizontal axis 5100 are represented intersecting at the lens center 1102 of the lens 1100. Originating from the lens center 1102, first and second upper speculum angle lines 5500 and 5501, respectively, are shown aligned with opposing ends of the upper speculum portion 1200. As well, first and second lower speculum angle lines 5600 and 5601, respectively, are similarly aligned with opposing ends of the lower speculum portion 1300.

The true horizontal axis 5100 creates two hemicircles of the lens: an upper portion and a lower portion. The true vertical axis 5000 also creates two hemicircles of the lens: a left portion and a right portion. Utilizing the true vertical axis 5000 and the various angle lines, several geometric angles between the various angle lines themselves and in relation to true vertical may be useful for defining some of the relative dimensions of the speculum portions. Upper speculum arc angle 1234 (short dashed arc) is determined between first and second upper speculum angle lines 5500, 5501. Lower speculum arc angle 1334 (short dashed arc) is determined between first and second lower speculum angle lines 5600, 5601.

Utilizing the same angle lines, minor arc circumferences for the upper speculum portion 1200 and the lower speculum portion 1300 may be defined. Along lens circumference 1106 (a circumference of lens 1100), an inner minor arc circumference 1238 (two short dash/long dash arc) of the upper speculum portion 1200 may be determined using first and second upper speculum angle lines 5500, 5501; an inner minor arc circumference 1338 of the lower speculum portion 1300 may also be determined using first and second lower speculum angle lines 5600, 5601. In a similar manner, outer minor arc circumference 1239 (two short dash/long dash arc) may be determined along a lead tip 1212 of an anterior tine 1210 of the upper speculum portion 1200 using first and second upper speculum angle lines 5500, 5501; outer minor arc circumference 1339 may be determined along a lead tip 1312 of an anterior tine 1310 of the lower speculum portion 1300 using first and second lower speculum angle lines 5600, 5601.

The upper speculum arc angle 1234 and the lower speculum arc angle 1334 may be utilized along with the true vertical axis 5000 to assist in describing the relative positions of the upper speculum portion 1200 and the lower speculum portion 1300 along the lens circumference 1106. A first upper speculum subarc angle 1235 is determined between the true vertical axis 5000 and first upper speculum angle line 5500; a second upper speculum subarc angle 1236 is determined between the second upper speculum angle line 5501 and the true vertical axis 5000. The two subarc angles 1235, 1236 add up to the upper speculum arc angle 1234. A first lower speculum subarc angle 1335 may be determined between the true vertical axis 5000 and first lower speculum angle line 5600; a second lower speculum subarc angle 1336 is determined between the second upper speculum angle line 5601 and the true vertical axis 5000. The two subarc angles 1335, 1336 add up to the lower speculum arc angle 1334.

Continuing with FIG. 1A, extending from the lens center 1102 are several radial lines. A lens radius 1104 reaches the lens circumference 1106, representing the maximum boundary of the lens 1100 at either a transition point 1110 to a speculum portion (dashed curves) or the circumferential edge 1108 of the lens 1100. Also extending from lens center 1102 is upper speculum tip radius 1232, which reaches to the lead tip 1212 of the anterior tine 1210 of the upper speculum portion 1200. The difference between the upper speculum tip radius 1232 and the lens radius 1104 is a height 1230 of the upper speculum portion 1200 as it extends away from the transition point 1110 of the lens circumference 1106. Lower speculum tip radius 1332 reaches to the lead tip 1312 of the anterior tine 1310 of the lower speculum portion 1300. The difference between the lower speculum tip radius 1332 and the lens radius 1104 is a height 1330 of the lower speculum portion 1300.

In FIG. 1B, several additional axis and angle lines may assist in defining useful attributes of the fully-integrated contact lens apparatus 1000. At lens center 1102 in FIG. 1B, a true central axis 5200 crosses through lens 1100. The true vertical axis 5000 and true center axis 5200 in FIG. 1B cross each other at a center 5402 of lens anterior surface circle 5400 and center 5302 of lens posterior surface circle 5300. An upper speculum transition line 5700 and lower speculum transition line 5701 both extend from centers 5302, 5402 through fully-integrated contact lens apparatus 1000. A lens arc angle 5705 is determined between upper speculum transition line 5700 and lower speculum transition line 5701.

For FIG. 1B, the lens posterior surface circle 5300 and lens anterior surface circle 5400 are displayed coaxially. Lens posterior surface circle 5300 has the center 5302, a radius 5304, and a circumference 5306 for describing at least a portion of the posterior surface curvature 1136. Lens anterior surface circle 5400 has the center 5402, a radius 5404, and a circumference 5406 for describing at least a portion of the anterior surface curvature 1126. In one or more embodiments, the center of the anterior surface circle and the center of the posterior surface circle are located in the same position. In such a configuration, the lens anterior surface circle 5400 and the lens posterior surface circle 5300 are coaxial and the resulting thickness of the lens would be even. In one or more embodiments, the center 5402 of the lens anterior surface circle 5400 and the center 5302 of the lens posterior surface circle 5300 are not located in the same position. In such a configuration, the thickness of the lens 1100 would be different between the center of the lens 1100 and the transition point to the speculum portions.

FIGS. 1B and 1C show points where differentiation of various thickness values on portions of the lens 1100 may be useful. FIG. 1B shows a central thickness 1140 and speculum transition point thickness 1144 for the lens 1100. FIG. 1C shows a circumferential edge thickness 1142 of the lens 1100.

FIGS. 1B and 1C also show configurational aspects for the upper and lower speculum portions 1200, 1300, respectively. The upper and lower anterior tines 1210, 1310 have anterior upper and lower lead tips 1212, 1312 with upper and lower anterior tine tip thicknesses 1214, 1314, respectively. The upper and lower posterior tines 1220, 1320 have posterior upper and lower lead tips 1222, 1322 with upper and lower posterior tine tip thicknesses 1224, 1324, respectively. A mouth 1226, 1326 is defined between each anterior lead tip 1212, 1312, and each corresponding posterior lead tip 1222, 1322 and each mouth 1226, 1326 has a mouth width 1228, 1328, respectively.

An upper speculum cup 1240 and the lower speculum cup 1340 are defined by the interior surfaces 1242, 1342 of the anterior tines 1210, 1310 and the posterior tines 1220, 1320, respectively. The bottom 1244, 1344 is defined at an intersection of the interior surfaces 1242, 1342 of the anterior tines 1210, 1310 and the posterior tines 1220, 1320 of the upper speculum cup 1240 and lower speculum cup 1340, respectively. The depths 1246, 1346 of the speculum cups 1240, 1340 are determined as measured from the speculum cup bottoms 1244, 1344 to the associated speculum cup mouths 1226, 1326, respectively.

In certain embodiments, the radius of the lens 1100 of the exemplary integrated contact lens apparatus 1000 is greater than the radius of cornea of the human eye to which the integrated contact lens apparatus is introduced. One of ordinary skill in the art appreciates that the human cornea is not usually circular on the exterior of the eye; rather, it is elliptical having a greater horizontal major axis diameter (typically about 11.75 millimeters (mm)) than a lesser vertical minor axis diameter (typically about 11.0 mm). As well, some people have a condition known as megalocornea or microcornea. In one or more embodiments the diameter of the lens portion of an integrated contact lens apparatus may be in a range of from about 8.00 mm to about 15.00 mm, such as from about 8.25, 8.50, 8.75, 9.00, 9.25, 9.50, 9.75, 10.00, 10.25, 10.50, 10.75, 11.00, 11.25, and 11.50 mm to about 11.75, 12.00, 12.25, 12.50, 12.75, 13.00, 13.25, 13.50, 13.75, 14.00, 14.25, 14.50, 14.75, and 15.00 mm inclusive and encompassing all such values in-between. Such a range of diameters may ensure coverage for most exceptional corneal conditions.

In one or more embodiments, a majority of the lens circumference 1106 is positioned along the sclera when the integrated contact lens apparatus 1000 is introduced onto the surface of the eye. In one or more embodiments, the entire lens circumference 1106 is positioned along the surface of the sclera when the integrated contact lens apparatus 1000 is introduced onto the surface of the eye. Not only does this ensure that the cornea is protected from contacting the posterior surface of the integrated contact lens 1000, but it also permits the circumferential edge 1108 of the lens 1100, the transition point 1110, and a portion of the exterior surface of the posterior tines 1220, 1320 of the lower and the upper speculum portions 1200, 1300 to contact with or fluidly couple to the surface of the sclera and not the cornea.

Although in FIG. 1A and similar figures show the lens 1100 as generally circular in nature as viewed anterior to posterior, and the lens 1100 is described generally in circle-related geometrical terms. This is only done for ease of description. It is appreciated by one of ordinary skill in the art that in other, non-pictured configurations that embodiment integrated contact lens apparatuses may comprise a non-circular lens, such as an elliptical, square, rectangular, or non-geometric shape, when viewed towards the anterior surface of the lens.

Returning to FIG. 1A, the upper speculum arc angle 1234, as measured from the center 1102 of the lens 1100, defines the relative circumferential length of the upper inner minor arc circumference 1238. Similarly, the lower speculum arc angle 1334 defines the relative circumferential length of the upper inner minor arc circumference 1338. In one or more embodiments, the upper speculum arc angle 1234 may be in a range of from about 10 degrees to about 65 degrees, such as from about 10, 15, 20, 25, 30, and 35 degrees to about 40, 45, 50, 55, 60, and 65 degrees inclusive and encompassing all such values in-between. In one or more embodiments, the lower speculum arc angle 1334 may be in a range of from about 10 degrees to about 65 degrees, such as from about 10, 15, 20, 25, 30, and 35 to about 40, 45, 50, 55, 60, and 65 degrees inclusive and encompassing all such values in-between. In one or more embodiments, the upper speculum arc angle 1234 and the lower speculum arc angle 1334 are about the same.

In FIG. 1A, the upper speculum portion 1200 has the upper speculum inner minor arc circumference 1238 where it is fully-integrated with the lens 1100 at lens circumference 1106. Similarly, the lower speculum portion 1300 has the lower speculum inner minor arc circumference 1338. In one or more embodiments, the integrated contact lens apparatus 1000 may have an upper speculum inner minor arc circumference in a range of from about 3.00 mm to about 10.00 mm, such as from about 3.00, 3.25, 3.50, 3.75, 4.00, 4.25, 4.50, 4.75, 5.00, 5.25, 5.50, 5.75, 6.00, and 6.25 mm to about 6.50, 6.75, 7.00, 7.25, 7.50, 7.75, 8.00, 8.25, 8.50, 8.75, 9.00, 9.25, 9.50, 9.75, and 10.00 mm inclusive and encompassing all such values in-between. In one or more embodiments, the integrated contact lens apparatus 1000 may have a lower speculum inner minor arc circumference in a range of from about 3.00 mm to about 10.00 mm, such as from about 3.00, 3.25, 3.50, 3.75, 4.00, 4.25, 4.50, 4.75, 5.00, 5.25, 5.50, 5.75, 6.00, and 6.25 mm to about 6.50, 6.75, 7.00, 7.25, 7.50, 7.75, 8.00, 8.25, 8.50, 8.75, 9.00, 9.25, 9.50, 9.75, and 10.00 mm inclusive and encompassing all such values in-between. In one or more embodiments, the upper inner minor arc circumference 1238 and the lower inner minor arc circumference 1338 are about the same.

The position of the upper speculum portion 1200 along the lens circumference 1106 may be described in relation to several axes, such as the true vertical axis 5000. In FIG. 1A, exemplary contact lens apparatus 1000 is shown having an upper speculum portion 1200 with an upper speculum arc angle 1234 that is bifurcated, that is, the first upper speculum subarc angle 1235 and second upper speculum subarc angle 1236 have approximately the same value. In one or more embodiments, the upper speculum portion 1200 is positioned such that it is centered relative to the true vertical axis in the upper hemicircle of the lens 1100. Similarly, in one or more embodiments, the lower speculum portion 1300 is positioned such that it is centered relative to the true vertical axis in the lower hemicircle of the lens 1100. In one or more embodiments, both the upper speculum portion 1200 and the lower speculum portion 1300 are positioned such that each are centered relative to the true vertical axis 5000 in opposing hemicircles of the lens 1100.

As previously described, the speculum tines have an exterior length that is measured from the transition point along the lens circumference from the lens 1100 to the speculum portions (for both upper and lower speculum portions 1200, 1300). In FIG. 1B, the upper speculum portion 1200 has the height 1230 as measured along the anterior tine 1210; the lower speculum portion 1300 has the height 1330 as measured along the anterior tine 1310. In one or more embodiments, the height of the upper speculum portion 1200 for the embodiment integrated contact lens apparatus is in a range of from about 1 mm to about 3 mm, such as from about 1.00, 1.25, 1.50, and 1.75 mm to about 2.00, 2.25, 2.50, 2.75, and 3.00 mm inclusive and encompassing all such values in-between. In one or more embodiments, the height of the lower speculum for the embodiment integrated contact lens apparatus is in a range of from about 1 mm to about 3 mm, such as from about 1.00, 1.25, 1.50, and 1.75 mm to about 2.00, 2.25, 2.50, 2.75, and 3.00 mm inclusive and encompassing all such values in-between. In one or more embodiments, the heights of the upper speculum and the lower speculum are about the same.

The speculum cups 1240, 1340 have a cup depth 1246, 1346, respectively, that is measured from the bottom 1244, 1344 of the cup 1240, 1340, respectively, where the corresponding anterior and the posterior tines meet along the inner surface of the speculum cup, to the mouth of the speculum cup, which is defined as the entry point to the speculum cup and is in between the tips of the anterior and posterior tines (for both upper and lower speculum portions 1200, 1300). In FIG. 1B, the upper speculum portion 1200 has a speculum cup depth 1246 that is measured from the upper speculum cup bottoms 1244 to the associated speculum cup mouths 1226; the lower speculum portion 1300 has a speculum cup depth 1346 that is measured from the lower speculum cup bottoms 1344 to the associated speculum cup mouth 1326. In one or more embodiments, the cup depth 1246 for the upper speculum portion 1200 for the integrated contact lens apparatus 1000 is in a range of from about 0.5 mm to about 2.5 mm, such as from about 0.50, 0.75, 1.00, and 1.25 mm to about 1.50, 1.75, 2.00, 2.25, and 2.50 mm inclusive and encompassing all such values in-between. In one or more embodiments, the cup depth 1346 for the lower speculum portion 1300 for the integrated contact lens apparatus 1000 is in a range of from about 0.5 mm to about 2.5 mm, such as from about 0.50, 0.75, 1.00, and 1.25 mm to about 1.50, 1.75, 2.00, 2.25, and 2.50 mm inclusive and encompassing all such values in-between. In one or more embodiments, the cup depth 1246 for the upper speculum portion 1200 and the cup depth 1346 for the lower speculum portion 1300 are about the same. The depth of each speculum cup should be sufficient to restrain at least a portion of the eyelid of the patient. As well, the depth of each speculum cup should be suitable to retain any eyelashes that may come loose during the procedure.

For simplicity of use and ease of manufacturing, one or more exemplary contact lens apparatuses 1000 may be configured with one or more relative symmetries, such as shown in FIG. 1A. In one or more embodiments, the upper speculum portion 1200 has symmetry with respect to the true vertical axis 5000 of the contact lens apparatus 1000. That is, along the true vertical axis 5000 the upper speculum portion 1200 is a mirror image of itself and has equivalent dimensions (for example, minor arc circumference, height). In one or more embodiments, the lower speculum portion 1300 has symmetry with respect to the true vertical axis 5000 of the contact lens apparatus. In one or more embodiments, the upper speculum portion 1200 and the lower speculum portion 1300 have symmetry with respect to the true horizontal axis 5100 of the contact lens apparatus 1000. That is, the upper speculum portion 1200 and the lower speculum portion 1300 are mirror images of one another along the true horizontal axis 5100.

A material of the integrated contact lens apparatus 1000 may comprise a homopolymer, a polymer blend, or a copolymer made from the reaction of one or more monomers. A homopolymer is a polymer only comprising the reaction product of one monomer. A copolymer is a polymer comprising the reaction product of two or more monomer. A copolymer, in some instances, may be the product of reacting two polymers, such as two different homopolymers, together, such as in block, graph, or cross linked (using a cross linking agent) configuration. A polymer blend is a physical blending, such as through melt extrusion or compounding, of two or more polymers; a blend does not necessarily require reaction between the two or more polymers.

Useful monomers for making one or more polymers for the integrated contact lens apparatus may include, but are not limited to, methacrylic acid (MAA), methyl methacrylate (MMA), vinyl alcohol (VA), diacetone acrylamide (DA), N-carboxyl vinyl ester (NCVE), phosphorylcholine (PC), ethylene glycol (EG), N,N-dimethyl acrylamide (DMAA), 2-hydroxyethyl methacrylate (HEMA), N-vinyl pyrrolidone (NVP), ethylene glycol dimethacrylate (EGDMA), triethylene glycol dimethacrylate (TEGDMA), tetraethyleneglycol dimethacrylate (TTEGMDA) dimethyl siloxane (DMS), tris(hydroxymethyl)aminomethane, 3-[tris (trimethylsiloxy)silyl]propyl methacrylate (TRIS), 3-[tris (trimethylsiloxy)silyl]propyl vinyl carbamate (TRIS-VC), and dimethyl siloxyl di(silylbutanol) bis(vinyl carbamate) (BVC).

Figure 2A:
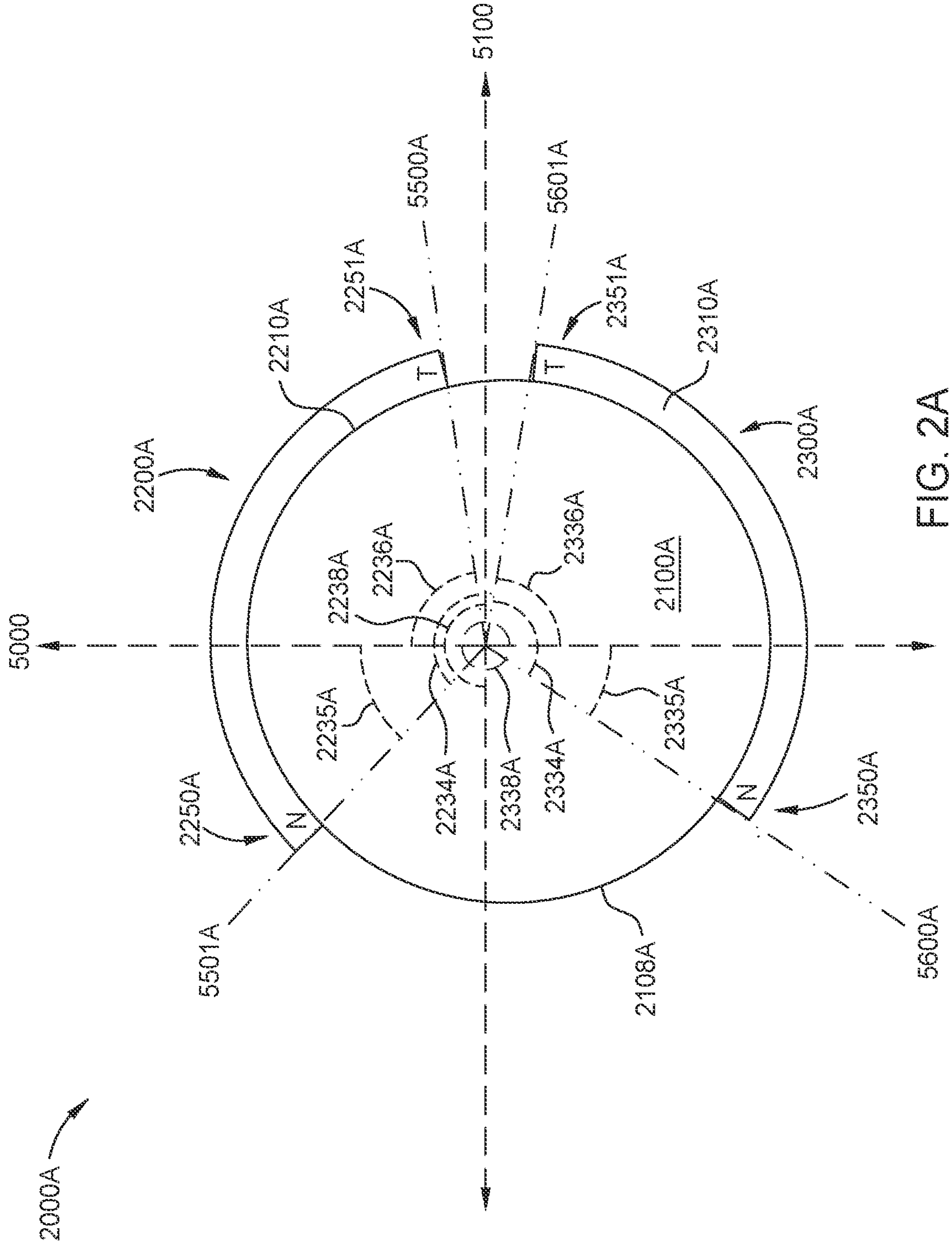
FIG. 2A provides a frontal view of a fully-integrated contact lens apparatus configured for introduction into a left eye, according to one or more embodiments.
Figure 2B:
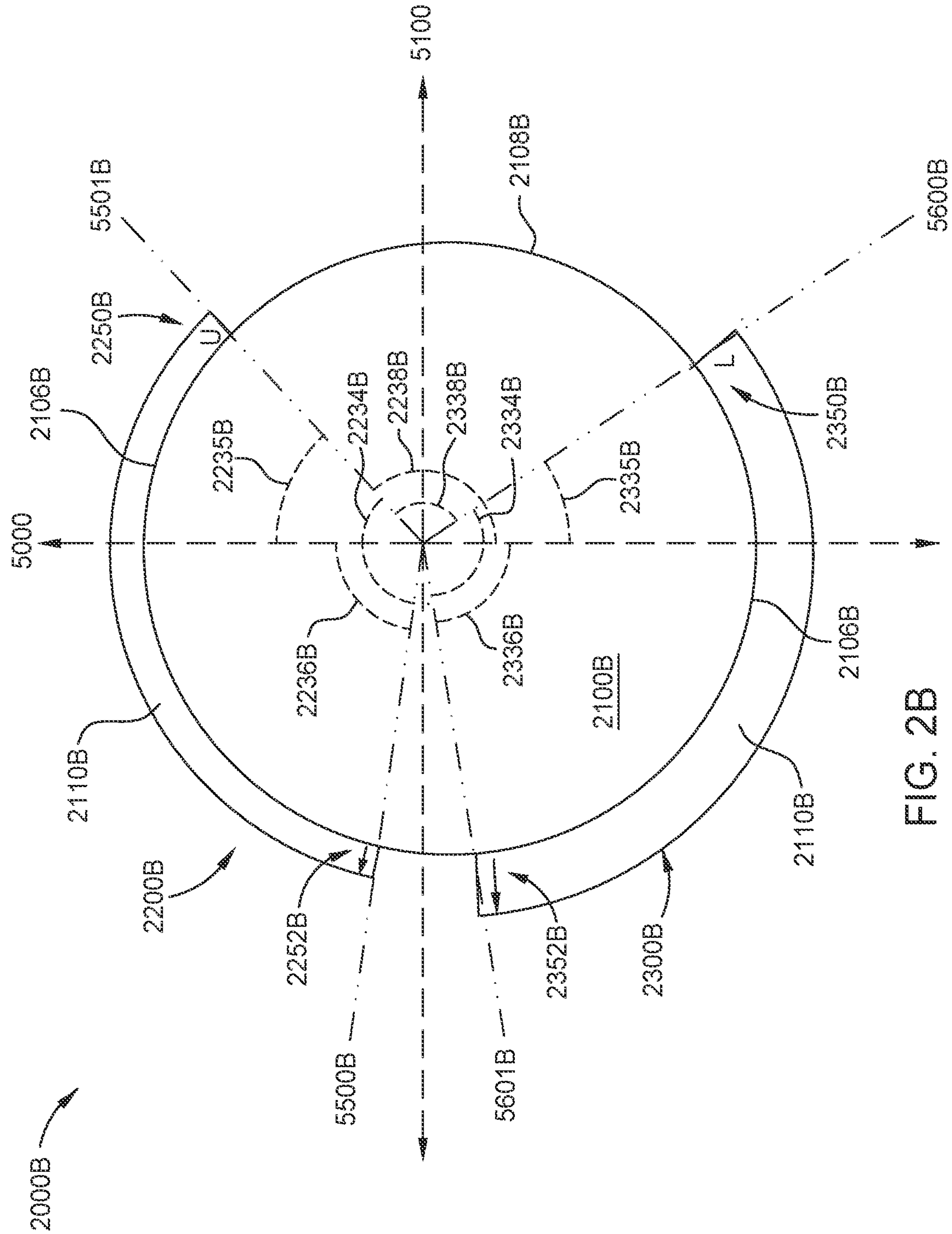
FIG. 2B provides a frontal view of a fully-integrated contact lens apparatus configured for introduction into a right eye, according to one or more embodiments.

FIG. 2A provides a frontal view of an exemplary fully-integrated contact lens apparatus 2000A configured for introduction into a left eye. FIG. 2B provides a frontal view of another exemplary fully-integrated contact lens apparatus 2000B configured for introduction into a right eye. FIGS. 2A and 2B and integrated contact lens apparatuses 2000A and 2000B, respectively, may appear similar to FIG. 1A and integrated contact lens apparatus 1000; however, there are important configuration differences in both the upper and lower speculum portion orientations that may make them, in some instances, more suitable for use in the left and right eyes, respectively, of a patient.

As similar to how the upper speculum arc angle 1234 and lower speculum arc angle 1334 for integrated contact lens apparatus 1000 define the circumferential length of the upper inner minor arc circumference 1238 and the circumferential length of the lower inner minor arc circumference 1338, respectively, in FIG. 2A, an upper speculum arc angle 2234A and a lower speculum arc angle 2334A for integrated contact lens apparatus 2000A define the circumferential length of an upper inner minor arc circumference 2238A and a lower inner minor arc circumference 2338A, respectively. In FIG. 2B, an upper speculum arc angle 2234B and a lower speculum arc angle 2334B for integrated contact lens apparatus 2000B define the circumferential length of an upper inner minor arc circumference 2238B and a lower inner minor arc circumference 2338B, respectively. In one or more embodiments, the upper speculum arc angle and the lower speculum arc angle of integrated contact lens apparatuses 2000A and/or 2000B are not about the same. In one or more embodiments, the upper inner minor arc circumference and the lower inner minor arc circumference of integrated contact lens apparatuses 2000A and/or 2000B are not about the same.

As previously utilized, an upper speculum portion along a lens circumference may be described in relation to several axes, such as the upper portion of the true vertical axis 5000. In FIG. 2A, exemplary contact lens apparatus 2000A is shown having upper speculum arc angle 2234A that is bifurcated, that is, upper speculum arc angle 2234A is split into the first upper speculum subarc angle 2235A and second upper speculum subarc angle 2236A; however, in this instance, because the upper speculum portion 2200A is not centered relative to the true vertical axis 5000, the first upper speculum subarc angle 2235A and second upper speculum subarc angle 2236A do not have about a similar value after bifurcation. In fact, one of ordinary skill in the art may note that the upper speculum portion 2200A is shifted towards stage right of the apparatus 2000A. Therefore, second upper speculum subarc angle 2236A has a greater value than first upper speculum subarc angle 2235A. In one or more embodiments, the upper speculum portion 2200A is positioned such that it is not centered relative to the true vertical axis 5000 in the upper hemicircle of the lens 2100A. FIG. 2B similarly shows where for contact lens apparatus 2000B, the first upper speculum subarc angle 2235A is greater than second upper speculum subarc angle 2236A because the upper speculum portion 2200B is shifted towards stage left of the apparatus 2000B.

In FIGS. 2A and 2B, one of ordinary skill in the art may also observe that in one or more embodiments, the lower speculum portion 2300A or 2300B is positioned such that it is not centered relative to the true vertical axis 5000 in the lower hemicircle of the lens 2100A or 2100B, respectively. In FIG. 2A, exemplary contact lens apparatus 2000A is shown having lower speculum arc angle 2334 that is bifurcated—that is, lower speculum arc angle 2334 is split into the first lower speculum subarc angle 2335A and second lower speculum subarc angle 2336A; however, in this instance, because the lower speculum portion 2200A is not positioned centered relative to the true vertical axis 5000, the first lower speculum subarc angle 2335A and second upper speculum subarc angle 2336A do not have about a similar value after bifurcation. In fact, one of ordinary skill in the art may note that the lower speculum portion 2300A is shifted towards stage right of the apparatus 2000A. Therefore, second upper speculum subarc angle 2336A has a greater value that first upper speculum subarc angle 2335A. In one or more embodiments, the lower speculum portion 2300A is positioned such that it is not centered relative to the true vertical axis 5000 in the lower hemicircle of the lens 2100A. FIG. 2B similarly shows where for embodiment contact lens apparatus 2000B, the first lower speculum subarc angle 2335A is greater than second upper speculum subarc angle 2336A because the upper speculum portion 2300B is shifted towards stage left of the apparatus 2000B.

For the integrated contact lens apparatuses 2000A, 2000B, there are distinct lack of symmetries that may be useful for customization of an integrated contact lens apparatus for a particular eye shape in general or specifically for a patient. In one or more embodiments, the upper speculum portion 2200A or 2200B does not have symmetry with respect to the true vertical axis 5000 of the contact lens apparatus. In one or more embodiments, the lower speculum portion 2300A or 2300B does not have symmetry with respect to the true vertical axis 5000 of the contact lens apparatus. In one or more embodiments, the upper speculum portion 2200A or 2200B and the lower speculum portion 2300A or 2300B do not have symmetry with respect to the true horizontal axis 5100 of the contact lens apparatus. That is, the upper speculum portions 2200A or 2200B and the lower speculum portions 2300A or 2300B are not mirror images of one another along the true vertical axis 5000. Again, this may be reflective of the different configurations of the upper and lower eyelids.

Even though there may be a lack of symmetry, the left and right eye configurations of the embodiment integrated contact lens apparatus do have certain angular relationships that may be characterized. This can be seen clearly in both FIGS. 2A and 2B, where both upper and lower speculum portions are shifted well stage right (in the case of FIG. 2A) and well stage left (in the case of FIG. 2B). In one or more embodiments, the integrated contact lens apparatus has both a first upper speculum subarc angle that is greater than a second upper speculum subarc angle and a first lower speculum subarc angle that is greater than a second lower speculum subarc angle. Such a configuration describes the right contact lens of embodiment integrated contact lens apparatus 2000B of FIG. 2B. In one or more embodiments, the integrated contact lens apparatus has both a first upper speculum subarc angle that is less than a second upper speculum subarc angle and a first lower speculum subarc angle that is less than a second lower speculum subarc angle. Such a configuration describes the left contact lens of embodiment integrated contact lens apparatus 2000A of FIG. 2A.

Both integrated contact lens apparatuses 2000A, 2000B show markings or labeling on the upper and/or lower speculum portions that have not previously shown in other figures but are envisioned. FIG. 2A shows integrated contact lens apparatus 2000A having lettering 2250A and letter 2251A present on the upper speculum portion 2200A at opposing ends; lettering 2350A and 2350B are present on the lower speculum portion 2300A in a similar manner. A practitioner of ordinary skill in the art may observe that the letter "N" is facing stage left of the viewer and a letter "T" is facing stage right for a left-eye oriented integrated contact lens apparatus. A practitioner of ordinary skill in the art may then surmise then that in this instance, the letters "N" may represent the term "nasal" and the letter "T" may represent the term "temporal".

FIG. 2B shows integrated contact lens apparatus 2000B having lettering 2250B ("U") present on the upper speculum portion 2200B; meanwhile, lettering 2350B ("L") is present on the lower speculum portion 2300B, which in combination with lettering 2250B, a practitioner of ordinary skill in the art may then surmise that these letters mean "upper" and "lower" speculum cups. Arrows 2252B, 2352B (→) pointing outward and stage left by view of the practitioner are also present on both the upper and lower speculum portions 2200B, 2300B. In combination with the lettering, a practitioner of ordinary skill in the art may then surmise that these arrows point towards the temporal side of the eye. Given that the marks and lettering are present on the anterior side of the integrated contact lens apparatus, the apparatus is configured for use in the right eye of a patient.

Such markings may assist the practitioner in identifying into which eye a particular integrated contact lens apparatus should be introduced, in which direction the temporal side or the nasal side of the integrated contact lens apparatus is directed, which side of the integrated contact lens apparatus is the anterior side (should the lens somehow become inverted, as can happen with soft contact lenses), which speculum portion is configured for the upper eyelid or the lower eyelid, and combinations thereof.

Markings may be applied to an embodiment integrated contact lens apparatus during or after its manufacture. For example, markings may be applied to the anterior surface of the integrated contact lens apparatus using a dye or ink application technique, such as electrostatic layering, onto the surface. In another example, markings may be etched or carved into the anterior surface of the integrated contact lens apparatus, such as by using an acidic solution, a mechanical material extracting apparatus, or a laser to create a pattern into the surface by removing material though thermal degradation. In another example, markings may be integrated into the material of the integrated contact lens apparatus during its manufacture. Such markings are often referred to as "mold marks" in the polymer processing industry and can either be raised from the surface (the mold has a reciprocal cavity permitting additional material to fill it) or depressed into the surface (the mold a reciprocal projection denying material in the mold form).

Figure 3A:
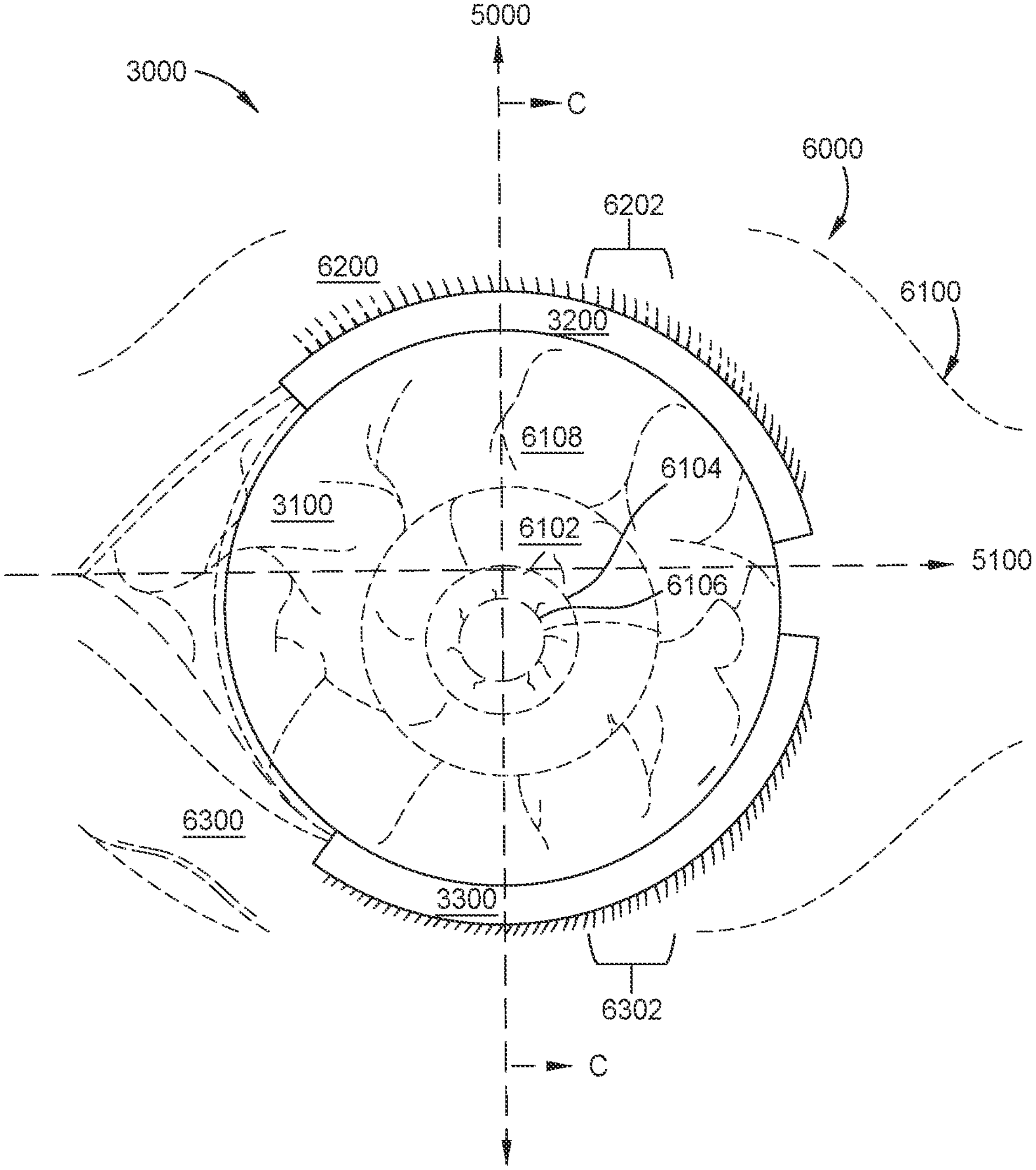
FIG. 3A provides a frontal view of a fully-integrated contact lens apparatus after introduction into an eye, according to one or more embodiments.

FIG. 3A provides a frontal view of a fully-integrated contact lens apparatus 3000 after introduction into an eye, according to one or more embodiments. Integrated contact lens apparatus 3000 appears configured similarly to integrated contact lens apparatus 2000A of FIG. 2A, that is, as an apparatus configured for introduction into a left eye. Integrated contact lens apparatus 3000 is seen as having been previously introduced into eye 6000. Behind lens 3100 can be seen features of the anterior portion 6100 of the eye 6000, including the cornea 6102, the iris 6104, and the pupil 6106. A significant portion of the sclera 6108 is also visible due to the restraining feature of the embodiment integrated contact lens apparatus 3000. Upper eyelid 6200 is partially restrained by the upper speculum portion 3200. Portions of the several upper eyelid eyelashes 6202 are seen restrained and protruding upwards from the upper speculum portion 3200, having been folded. Lower eyelid 6300 is also shown partially restrained by the lower speculum portion 3300 and with folded downward-projecting eyelashes 6302.

Figure 3B:
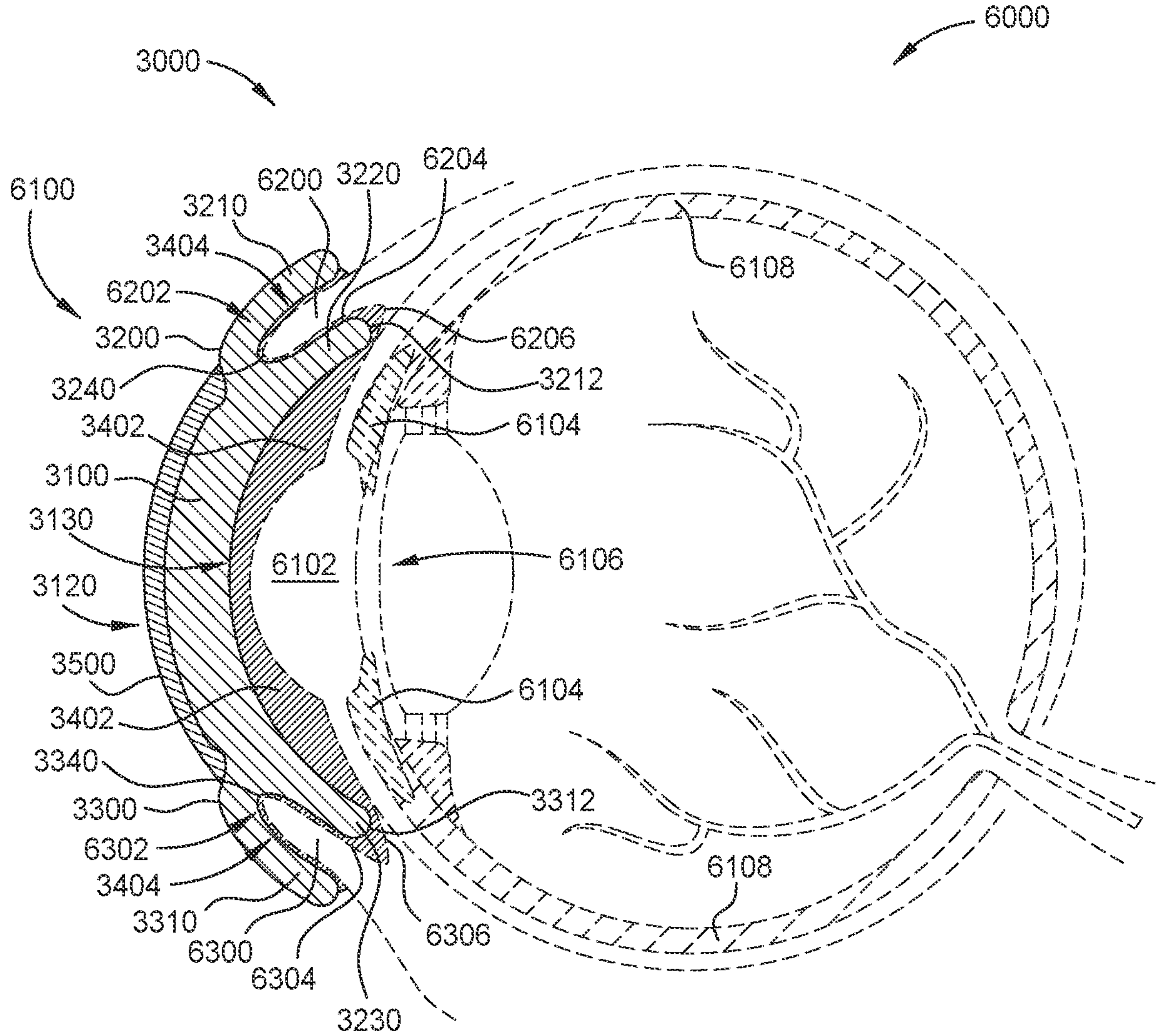
FIG. 3B provides a cross-sectional side view of a fully-integrated contact lens apparatus introduced into an eye as viewed along sight lines CC of FIG. 3A, according to one or more embodiments.

FIG. 3B provides a cross-sectional side view of the fully-integrated contact lens apparatus 3000 introduced into the eye 6000 as viewed along sight lines CC of FIG. 3A. As better appreciated from this vantage, both the upper and lower eyelids 6200, 6300, are fully restrained within upper and lower speculum cups 3240, 3340, respectively. The upper posterior tine 3220 is positioned in between and frictionally coupled to both the upper palpebral conjunctiva 6204 and upper bulbar conjunctiva 6206; lower posterior tine 3320 is positioned in between and frictionally coupled to both the upper palpebral conjunctiva 6304 and upper bulbar conjunctiva 6306. The position and the frictional couplings should not only help to maintain the integrated contact lens apparatus in its position over the cornea and the anterior portion of the sclera but also restrain both the upper eyelid and the lower eyelid from inadvertent vertical motions.

In FIG. 3B, it is shown that there is an ocular fluid buffer layer 3402 disposed between the posterior lens surface 3130 and both the cornea 6102 and a portion of the sclera 6108. The ocular fluid buffer layer 3402 is contained behind the posterior lens surface 3130 for most if not all of the lens 3100 and is retained from loss by a combination of the circumferential edge of the lens 3100 and the posterior exterior surface of the posterior tines 3220, 3320 of both the upper speculum portion 3200 and lower speculum portion 3300, respectively, of the integrated contact lens apparatus 3000.

Although not wanting to be bound by theory, it is believed that the ocular fluid buffer layer 3402 may naturally form between the eye 6000 and the integrated contact lens apparatus 3000 during use thereof. For example, the ocular fluid buffer 3402 layer may comprise natural fluids that accumulate from the eye 6000, such as moisture from secreted tears of the patient. In one or more embodiments, the ocular fluid buffer 3402 layer may also comprise a synthetic buffer fluid. For example, the ocular fluid buffer layer 3402 may comprise a buffer fluid, such as a buffer solution, introduced by the examiner to a surface the eye 6000 or posterior lens surface 3130 prior to placement of the integrated contact lens apparatus 3000. In combination with natural fluids present, a buffer fluid may be useful as part of the ocular fluid buffer layer 3402 during the examination process to protect the cornea 6102 and portions of the sclera 6108 present behind the lens 3100 of the apparatus 3000.

As will be described further, a buffer fluid may be introduced to either or both the surface of the eye 6000 or the posterior lens surface 3130 before application of an contact lens apparatus 3000 to the surface of the eye 6000. Introducing a buffer fluid to the posterior lens surface 3130 of the integrated contact lens apparatus 3000 permits the wetting of the posterior lens surface 3130 in preparation for introduction onto the eye 6000. This may permit lubrication of the posterior lens surface 3130 as well as hydration of the lens 3100 of the integrated contact lens apparatus 3000. Introducing the buffer fluid also may permit an amount of accumulated buffer fluid on the posterior lens surface 3130 to become trapped in the void formed by the posterior surface 3130 and the outer surface of the cornea 6102 and portions of the sclera 6108 when the integrated contact lens 3000 is introduced to the eye 6000, forming an ocular fluid buffer layer 3402.

A buffer solution may comprise a mild pH (about 7.0), slightly saline solution. In one or more embodiments, the buffer solution may comprise an artificial tears solution, such as, but not limited to, hydroxypropyl methylcellulose in distilled water. In one or more embodiments, the buffer solution may comprise a wetting agent. In one or more embodiments, the buffer solution may comprise a lubricating agent. In one or more embodiments, the buffer solution may comprise an anti-inflammatory agent. The anti-inflammatory agent may be specifically chosen for use with the cornea 6102, the sclera 6108, or both.

In FIG. 3B, it is also shown in integrated contact lens apparatus 3000 that there is a protective anterior surface coating 3500. The protective anterior surface coating 3500 shown is not only coupled to the anterior surface 3120 of the lens 3100, but also to at least a portion of each of the exterior surfaces of the anterior tines 3210, 3310. Coupling to both the lens 3100 and at least part of the anterior tines 3210,3310 of the upper and lower speculum portions 3200, 3300 may provide rigidity in form for the integrated contact lens apparatus 3000, which may make it easier for a practitioner to handle and secure it in the eye 6000 of a patent. The protective anterior surface coating 3500 in some instances may extend all the way through the tips 3212, 3312 of the anterior tines 3210, 3310, respectively, although this is not shown for integrated contact lens apparatus 3000 in FIG. 3B. In one or more embodiments, the protective anterior surface coating 3500 is coupled to the anterior lens surface 3120 of the integrated contact lens apparatus 3000. In one or more embodiments, the protective anterior surface coating 3500 is coupled to at least a portion of the exterior surface of the anterior tine 3210 of the upper speculum portion 3200 of the integrated contact lens apparatus 3000. In one or more embodiments, the protective anterior surface coating 3500 is coupled to at least a portion of the exterior surface of the anterior tine 3310 of the lower speculum portion 3300 of the integrated contact lens apparatus 3000.

In one or more embodiments, the composition of the protective anterior surface coating 3500 for the integrated contact lens apparatus 3000 comprises a material that is more rigid than the material comprising the remainder of the integrated contact lens apparatus. For example, the protective anterior surface coating 3500 may comprise a homopolymer, a polymer blend, or a copolymer comprising poly (methyl)methacrylate (PMMA). Such a material may provide to the protective anterior surface coating 3500 a rigidity of structure to maintain the overall shape of the integrated contact lens apparatus 3000, strength to restrain inadvertent vertical eyelid movement, minimal fluid permeability to prevent the loss of fluids through the layer, and visual clarity to permit examination.

The protective anterior surface coating 3500 may be coupled or connected to the anterior surface(s) of the integrated contact lens apparatus 3000 using techniques known to one of ordinary skill in the art of polymer processing and contact manufacturing, including, but not limited to, adhesion, spray coating, injection molding, and reactive molding. In one or more embodiments, a coupling layer adheres the anterior surface 3120 of the lens 3100 and the protective anterior surface coating 3500 of the integrated contact lens apparatus 3000 together.

Also shown in FIG. 3B is a restraining material 3404 present in both the upper speculum cup 3240 surrounding the upper eyelid 6200 and the lower speculum cup 3340 and lower eyelid 6300. In one or more embodiments, a restraining material 3404 is present in the upper speculum cup 3240. In one or more embodiments, a restraining material 3404 is present in the lower speculum cup 3340.

Useful purposes for the restraining material 3404 in either or both the upper and lower speculum cup 3240, 3340 are several-fold. When an eyelid is introduced into a speculum cup, one or more of the eyelashes may detach from an eyelid. In such an instance, the restraining material 3404 may retain the detached eyelash from egressing from the speculum cup before or during the examination and moving onto the anterior surface or (worse) the posterior surface of the integrated contact lens apparatus 3000. The restraining material 3404 may be a fluid and have a viscosity significant enough that the restraining material 3404 functions as a light fluid adhesive between the eyelid and the speculum cup. The viscosity of the restraining material 3404 may be great enough such that if there is eyelid movement in a vertical direction, then the corresponding speculum cup moves at least in part with the eyelid without the eyelid touching the inner surface of the anterior or posterior tines or the bottom of the speculum cup. The restraining material 3404 may also prevent portions of the ocular fluid buffer layer 3402 from egressing from behind the integrated contact lens apparatus 3000 by way of the restrained portions of the conjunctiva, thereby acting as a fluidic barrier to the prior-described ocular fluid buffer layer. As to be described, the restraining material 3404 may comprise, consist essentially of, or consist of additives or agents that may assist in preventing disease transmission through or injury to the sclera and conjunctiva. The retraining material 3404 may also prevent natural secretions, such as tears from a patient from flowing around the posterior tine of the speculum cup and into the ocular fluid buffer layer.

The restraining material 3404 may take the form of a fluid, such as a highly viscous fluid or "jelly", or a semi-solid material, such a polymeric gel, which is a three dimensional partially cross-linked polymer network that can undergo significant deformation. In one or more embodiments, the viscosity of the restraining material 3404 is greater than that of a buffer solution.

In one or more embodiments, the restraining material 3404 may comprise an anti-inflammatory agent. In one or more embodiments, the restraining material 3404 may comprise an anesthetic agent. An anti-inflammatory or anesthetic agent may be utilized to prevent immediate or lasting irritation to the conjunctiva, which are mucus membranes, thereby increasing patient comfort. In one or more embodiments, the restraining material 3404 may comprise an anti-bacterial agent. In one or more embodiments, the restraining material 3404 may comprise an anti-viral agent.

Figure 4A:
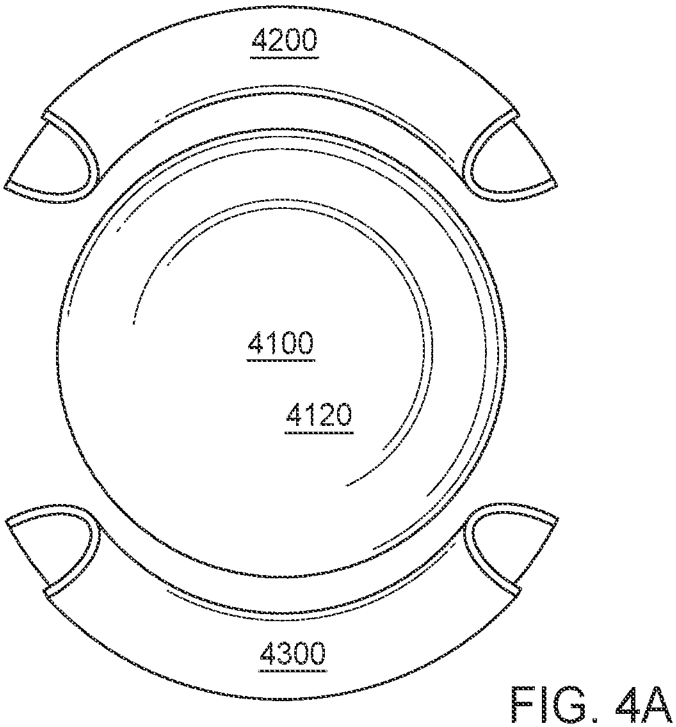
FIG. 4A provides a front view of several components of a contact lens apparatus prior to integration into an integrated contact lens apparatus, according to one or more embodiments.
Figure 4B:
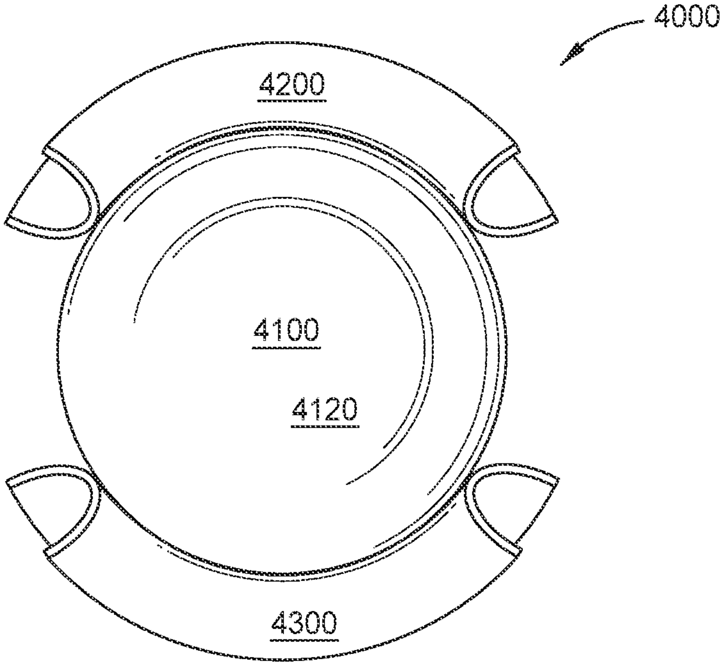
FIG. 4B provides a front view of an integrated contact lens apparatus after integration of the components provided in FIG. 4A, according to one or more embodiments.

FIG. 4A provides a front view of several components of a contact lens apparatus prior to integration into an integrated contact lens apparatus 4000 (shown in FIG. 4B). Lens 4100 has an anterior surface 4120. Separate upper speculum portion 4200 is awaiting coupling or connection to an upper portion of the lens 4100. Separate lower speculum portion 4300 is awaiting coupling or connection to a lower portion of the lens 4100. Upon at least coupling of the upper speculum portion 4200 and the lower speculum portion 4300 to the lens 4100, an integrated contact lens apparatus 4000 is formed. Practically, the upper and lower speculum portions and the lens may be manufactured at different times or at different locations. Then, such components may be assembled together into the integrated contact lens apparatus by connection or coupling through either or a combination of manual or automated processes.

In one or more embodiments, the upper speculum portion 4200 comprises a first material and the lens 4100 comprises a second material, where the first material and the second material are different. In one or more embodiments, the upper speculum portion 4200 comprises a first material and the lower speculum portion 4300 comprises a second material, where the first material and the second material are different.

FIG. 4B provides a front view of the integrated contact lens apparatus 4000 after integration of the components provided in FIG. 4A. Integrated contact lens apparatus 4000 is formed from the permanent coupling of the separate component parts of lens 4100, upper speculum portion 4200, and lower speculum portion 4300 into the one Unless defined otherwise, all technical and scientific terms used have the same meaning as commonly understood by one of ordinary skill in the art to which these systems, apparatuses, methods, processes and compositions belong.

The singular forms "a," "an," and "the" include plural referents, unless the context clearly dictates otherwise.

As used here and in the appended claims, the words "comprise," "has," and "include" and all grammatical variations thereof are each intended to have an open, non-limiting meaning that does not exclude additional elements or steps.

Embodiments of the present disclosure may suitably "comprise", "consist" or "consist essentially of" the limiting features disclosed, and may be practiced in the absence of a limiting feature not disclosed.

"Optionally" means that the subsequently described event or circumstances may or may not occur. The description includes instances where the event or circumstance occurs and instances where it does not occur.

When the word "approximately" or "about" are used, this term may mean that there can be a variance in value of up to ±10%, of up to 5%, of up to 2%, of up to 1%, of up to 0.5%, of up to 0.1%, or up to 0.01%.

Ranges may be expressed as from about one particular value to about another particular value, inclusive. When such a range is expressed, it is to be understood that another embodiment is from the one particular value to the other particular value, along with all particular values and combinations thereof within the range.

As used, terms such as "first" and "second" are arbitrarily assigned and are merely intended to differentiate between two or more components of a system, an apparatus, or a composition. It is to be understood that the words "first" and "second" serve no other purpose and are not part of the name or description of the component, nor do they necessarily define a relative location or position of the component. Furthermore, it is to be understood that that the mere use of the term "first" and "second" does not require that there be any "third" component, although that possibility is contemplated under the scope of the various embodiments described.

Although only a few example embodiments have been described in detail, those skilled in the art will readily appreciate that many modifications are possible in the example embodiments without materially departing from the disclosed scope as described. Accordingly, all such modifications are intended to be included within the scope of this disclosure as defined in the following claims. In the claims, means-plus-function clauses are intended to cover the structures described as performing the recited function and not only structural equivalents, but also equivalent structures. For example, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6, for any limitations of any of the claims, except for those in which the claim expressly uses the words 'means for' together with an associated function.

What is claimed is:

1. An integrated contact lens apparatus, comprising:
a single piece of polymer material comprising:
a contact lens portion having a circumferential edge, an anterior surface, and a posterior surface, wherein the contact lens portion has a center traversed by a true horizontal axis that defines an upper portion and a lower portion of the circumferential edge;
an upper speculum portion extending from the contact lens portion along the upper portion of the circumferential edge for an upper inner minor arc circumference, the upper speculum portion comprising a posterior tine that at least partially defines an upper speculum cup; and
a lower speculum portion extending from the contact lens portion along the lower portion of the circumferential edge for a lower inner minor arc circumference, the lower speculum portion comprising a posterior tine that that at least partially defines a lower speculum cup,
wherein the upper speculum cup is configured to receive and retain an upper eyelid in a retracted manner when the posterior tine of the upper speculum portion is positioned between portions of an upper conjunctiva, and
wherein the lower speculum cup is configured to receive and retain a lower eyelid in a retracted manner when the posterior tine of the lower speculum portion is positioned between portions of a lower conjunctiva.

2. The integrated contact lens apparatus of claim 1, wherein a diameter of the contact lens portion as measured through the center is in a range of from about 8.00 mm (millimeters) to about 15.00 mm.

3. The integrated contact lens apparatus of claim 1, wherein an upper speculum arc angle as measured from the center is in a range of from about 10° (angle degrees) to about 65°.

4. The integrated contact lens apparatus of claim 1, wherein a lower speculum arc angle as measured from the center is in a range of from about 10° to about 65°.

5. The integrated contact lens apparatus of claim 1, wherein the upper speculum portion includes an upper speculum inner minor arc circumference having an arc length in a range of from about 3.00 mm to about 10.00 mm.

6. The integrated contact lens apparatus of claim 1, wherein the lower speculum portion includes a lower speculum inner minor arc circumference having an arc length in a range of from about 3.00 mm to about 10.00 mm.

7. The integrated contact lens apparatus of claim 1, wherein the upper speculum portion has an anterior tine height in a range of from about 1.00 mm to about 3.00 mm.

8. The integrated contact lens apparatus of claim 1, wherein the lower speculum portion has an anterior tine height in a range of from about 1.00 mm to about 3.00 mm.

9. The integrated contact lens apparatus of claim 1, wherein the upper speculum cup has a cup depth in a range of from about 0.5 mm to about 2.5 mm.

10. The integrated contact lens apparatus of claim 1, wherein the lower speculum cup has a cup depth in a range of from about 0.5 mm to about 2.5 mm.

11. The integrated contact lens apparatus of claim 1, wherein the upper speculum portion has symmetry with respect to a true vertical axis of the lens portion, wherein the true vertical axis traverses the center.

12. The integrated contact lens apparatus of claim 1, wherein the lower speculum portion has symmetry with respect to a true vertical axis of the lens portion, wherein the true vertical axis traverses the center.

13. The integrated contact lens apparatus of claim 1, wherein the upper speculum portion and the lower speculum portion have symmetry with one another in relation to the true horizontal axis.

14. The integrated contact lens apparatus of claim 1, where the polymer material is formed from a polymerization reaction of one or more monomers selected from the group consisting of methacrylic acid (MAA), methyl methacrylate (MMA), vinyl alcohol (VA), diacetone acrylamide (DA), N-carboxyl vinyl ester (NCVE), phosphorylcholine (PC), ethylene glycol (EG), N,N-dimethyl acrylamide (DMAA), 2-hydroxyethyl methacrylate (HEMA), N-vinyl pyrrolidone (NVP), ethylene glycol dimethacrylate (EGDMA), triethylene glycol dimethacrylate (TEGDMA), tetraethyleneglycol dimethacrylate (TTEGMDA) dimethyl siloxane (DMS), tris (hydroxymethyl)aminomethane, 3-[tris(trimethylsiloxy) silyl]propyl methacrylate (TRIS), 3-[tris(trimethylsiloxy) silyl]propyl vinyl carbamate (TRIS-VC), and dimethyl siloxyl di(silylbutanol) bis(vinyl carbamate) (BVC).

15. An integrated contact lens apparatus, comprising:

a contact lens portion comprising a polymer material, the contact lens portion having a circumferential edge, an anterior surface, and a posterior surface, wherein the contact lens portion has a center traversed by a true horizontal axis that defines an upper portion and a lower portion of the circumferential edge;

an upper speculum portion comprising the polymer material, the upper speculum portion connected to the contact lens portion using an adhesive along the upper portion of the circumferential edge for an upper inner minor arc circumference, the upper speculum portion comprising a posterior tine that at least partially defines an upper speculum cup; and a lower speculum portion comprising the polymer material, the lower speculum portion connected to the contact lens portion using an adhesive along the lower portion of the circumferential edge for a lower inner minor arc circumference, the lower speculum portion comprising a posterior tine that that at least partially defines a lower speculum cup;

wherein the upper speculum cup is configured to receive and retain an upper eyelid in a retracted manner when the posterior tine of the upper speculum portion is positioned between portions of an upper conjunctiva, and wherein the lower speculum cup is configured to receive and retain a lower eyelid in a retracted manner when the posterior tine of the lower speculum portion is positioned between portions of a lower conjunctiva.

16. An integrated contact lens apparatus, comprising:

a contact lens portion comprising a polymer material, the contact lens portion having a circumferential edge, an anterior surface, and a posterior surface, wherein the contact lens portion has a center traversed by a true horizontal axis that defines an upper portion and a lower portion of the circumferential edge;

an upper speculum portion comprising the polymer material, the upper speculum portion connected to the contact lens portion using a weld along the upper portion of the circumferential edge for an upper inner minor arc circumference, the upper speculum portion comprising a posterior tine that at least partially defines an upper speculum cup; and a lower speculum portion comprising the polymer material, the lower speculum portion connected to the contact lens portion using a weld along the lower portion of the circumferential edge for a lower inner minor arc circumference, the lower speculum portion comprising a posterior tine that that at least partially defines a lower speculum cup;

wherein the upper speculum cup is configured to receive and retain an upper eyelid in a retracted manner when the posterior tine of the upper speculum portion is positioned between portions of an upper conjunctiva, and wherein the lower speculum cup is configured to receive and retain a lower eyelid in a retracted manner when the posterior tine of the lower speculum portion is positioned between portions of a lower conjunctiva.

* * * * *